US 6,685,969 B2

(12) United States Patent
Van Scoik et al.

(10) Patent No.: US 6,685,969 B2
(45) Date of Patent: Feb. 3, 2004

(54) TREATMENT FOR ECTOPARASITES

(75) Inventors: Kurt G. Van Scoik, Germantown, TN (US); Marcia S. Schlesinger, Germantown, TN (US)

(73) Assignee: Schering-Plough HealthCare Products, Inc., Memphis, TN (US)

( * ) Notice: Subject to any disclaimer, the term of this patent is extended or adjusted under 35 U.S.C. 154(b) by 0 days.

(21) Appl. No.: 09/878,702

(22) Filed: Jun. 11, 2001

(65) Prior Publication Data
US 2002/0197332 A1 Dec. 26, 2002

(51) Int. Cl.$^7$ .............................. A61K 7/00; A61K 7/06; A61K 33/06; A61K 33/00; A01N 59/00

(52) U.S. Cl. ..................... 424/724; 424/405; 424/600; 424/617; 424/682; 424/684; 424/688; 424/689; 424/690; 424/691; 424/692; 424/693; 424/694; 424/698; 424/DIG. 10; 514/770; 514/875; 514/919; 514/957; 43/132.1

(58) Field of Search ................ 424/405, 682, 424/684, 724, 600, 617, 688, 689–694, 698, DIG. 10; 43/132.1; 119/664; 514/875, 770, 919, 957

(56) References Cited

U.S. PATENT DOCUMENTS

| 3,250,880 A | 5/1966 | Menkart et al. ............... 167/85 |
| 4,379,143 A | 4/1983 | Sherry et al. ................ 424/154 |
| 4,626,550 A | 12/1986 | Hertzenberg ................ 514/770 |
| 5,261,427 A | * 11/1993 | Dolev ........................ 132/200 |
| 5,576,007 A | * 11/1996 | Ikeda et al. ................. 424/408 |
| 5,628,332 A | 5/1997 | Debourg et al. ............. 132/118 |
| 5,858,383 A | 1/1999 | Precopio ..................... 424/405 |
| 6,139,859 A | 10/2000 | Precopio ..................... 424/406 |
| 6,265,384 B1 | 7/2001 | Pearlman ..................... 514/31 |
| 6,303,581 B2 | 10/2001 | Pearlman ..................... 514/31 |

FOREIGN PATENT DOCUMENTS

| WO | WO 92/20308 | 11/1992 |
| WO | WO 99/18800 | 4/1999 |
| WO | WO 00/05945 | 2/2000 |

OTHER PUBLICATIONS

Tarshis, I. Barry, "The Use of Silica Aerogel Compounds for the Control of Ectoparasites," Proceedings of the Animal Care Panel, vol. 12, No. 5, pp. 217–258, Dec. 1962.*
Chemical Abstracts 56:9477 (1962).*
Chemical Abstracts 65:24527 (1966).*
Abstract of JP1029256 from esp@cenet (Jan. 1989).
Abstract of JP2001190204 from esp@cenet (Jul. 2001).

* cited by examiner

*Primary Examiner*—John Pak
(74) *Attorney, Agent, or Firm*—Robert A. Franks

(57) ABSTRACT

Ectoparasites, such as fleas, ticks, mites and lice, are removed from a human or animal host after applying a composition that causes the temperature of the treated area to become higher or lower than normal. In one embodiment, treatment is effected by applying a composition that releases heat when contacted with water. The elevated or decreased temperature immobilizes the parasites and facilitates their mechanical removal, such as by combing.

20 Claims, No Drawings

TREATMENT FOR ECTOPARASITES

INTRODUCTION TO THE INVENTION

The present invention relates generally to the removal of ectoparasites from the bodies of humans and animals, and more particularly to a topical treatment to facilitate such removal.

Ectoparasite infestation of humans and animals is a serious health problem throughout the world. Of particular importance as a public health issue is pediculosis, or infestations with lice, which are pervasive among children and can quickly be spread in a school setting. A very common parasite is *Pediculus humanus* var *capitis*, the common head louse, although there are other important parasites, including *Pthirus pubis* (the pubic louse) and *Pediculus humanus* var *corporis* (the body louse). Infestations are frequently accompanied by itching and skin damage. Infections and other adverse conditions may occur when the skin is scratched in an attempt to relieve the itching. Further, lice are known to be capable of transmitting serious diseases, including trench fever, relapsing fever and typhus.

Pediculosis is most frequently treated by applying pesticidal compositions, such as lotions or shampoos, to the affected body areas, such as the hair, and then exhaustively combing with a fine-tooth comb made especially for the purpose of removing nits. Commercially available preparations may include as their active ingredients pyrethrins, piperonyl butoxide, malathion, lindane or permethrins, many of which unfortunately have neurotoxic properties, are readily absorbed through the skin and therefore can establish undesirable systemic concentrations. It is perceived that the effectiveness of pesticides has recently diminished, as the parasites appear to continually become more resistant to their action. The resistance may be aggravated by small amounts of residual pesticide on the treated areas, following the procedure. This resistance also contributes to an increased opportunity for toxic systemic exposure to the active ingredients, since the preparations must be applied repeatedly to obtain an eradication of the infestation. Further, the pesticides do not usually kill the parasite's eggs that may be present on a host, so the tedious mechanical removal techniques must also be used.

Successful ectoparasite infestation treatment involves not only removal of pests from the host, but also a concurrent removal of the pests from the environment. It is necessary to scrupulously clean clothing, bed linens, etc. to avoid reinfestation. Of course, if other residents of the household are hosting ectoparasites, the probability of eradicating them on an individual is quite low.

DiNapoli et al., "Eradication of Head Lice with a Single Treatment," *American Journal of Public Health*, Vol. 78, pages 978–980, 1988, reported a study in which 7 percent of patients treated with a commercial 1 percent permethrin cream rinse, and 16 percent of patients treated with a commercial product containing 0.3 percent pyrethrins, 3 percent piperonyl butoxide, 1.2 percent petroleum distillate and 2.4 percent benzyl alcohol, experienced adverse reactions including pruritis, erythema, tingling, rash and other conditions. Further, by 14 days following treatment 38 percent of the patients treated with the pyrethrin product were found to host live lice, considered a treatment failure. Permethrin is described as having residual activity on the hair for up to two weeks.

R. J. Roberts et al., "Comparison of Wet Combing with Malathion for Treatment of Head Lice in the UK: a Pragmatic Randomised Controlled Trial," *The Lancet*, Vol. 356, pages 540–544, 2000, report that mechanical removal of lice with a commercial comb every 3–4 days for two weeks gave a "cure" rate of only 38 percent, while two treatments with 0.5 percent malathion lotion seven days apart gave a "cure" rate of 78 percent.

Published results for the various topical pesticidal treatments were compared by. R. H. Vander Stichele et al., "Systematic Review of Clinical Efficacy of Topical Treatments for Head Lice," *British Medical Journal*, Vol. 311, pages 604–608, 1995. It was concluded that only permethrin had sufficient evidence of efficacy.

There are other approaches to treating the infestations, including the application of heavy, oily substances such as mineral oil, petrolatum, mayonnaise and the like in an attempt to suffocate the ectoparasites, but these have not been found particularly effective, esthetically pleasing or convenient. One major disadvantage of such treatments is the prolonged time (usually several hours) required to achieve suffocation, after the agent has been applied.

The suffocation technique has been refined, such as by the approach of U.S. Pat. No. 6,139,859 to Precopio which utilizes air-impermeable water-dispersible liquid compositions containing surface active agents. Another type of treatment refinement is the technique of Pearlman et al. in PCT International Publication WO 99/18800, involving the topical application of surfactant substances as "pediculostatic agents" which immobilize the parasites to permit their removal by combing.

Various cosmetic products that generate heat in the presence of moisture have been reported. U.S. Pat. No. 3,250,680 to Menkart et al. describes cleaning and other liquid, creamy or pasty consumer product compositions that contain the alkali metal aluminosilicate called Molecular Sieve 5A; when applied following contact with water, the compositions are said to impart a pleasing warmth to the skin. U.S. Pat. No. 4,379,143 to Sherry et al. is directed toward analgesic balms, ointments or lotions that contain activated zeolites which hydrate exothermically using skin moisture and can thus provide heat to relieve muscle pain and the like.

The application of very hot water can kill head lice on articles such as combs and brushes. However, the temperatures and times required for efficacy would not be tolerable on the skin of a person or animal.

It remains desirable to have a treatment for ectoparasitic infestations which is efficacious, acts rapidly and does not generate great discomfort or require any exposure of the host to toxic agents.

SUMMARY OF THE INVENTION

The present invention is a treatment for ectoparasitic infestations, particularly those involving fleas, ticks, mites or lice, comprising establishing temperature conditions above or below the normal range of skin temperatures in the infested area, for a time sufficient to immobilize or kill the ectoparasites, then removing the pests by mechanical means such as combing.

In one embodiment, the invention involves compositions which generate elevated temperatures when contacted with water, such as is present in moistened hair or skin. The elevated temperatures are maintained for a time sufficient to cause immobilization and/or mortality of the parasites, facilitating their mechanical removal by combing and other techniques.

Treatment can be conducted using a composition which generates heat, when contacted with water. In one embodiment, the composition is a particulate solid, a semi-solid or a fluid containing substantially no aqueous matter, or in some instances only a small amount of water, and which contains a particulate inorganic substance that can react exothermally with water. Examples of suitable substances are aluminosilicates and alkaline earth metal oxides. The exothermic reaction is not necessarily one which results in formation of any new chemical compound, but can be an absorption-type reaction.

In another embodiment, the temperature is reduced below the usual range of skin temperatures for the infested area.

DETAILED DESCRIPTION OF THE INVENTION

The invention will be described primarily as it relates to the reduction of human head lice infestations, although those skilled in the art will recognize its applicability to other ectoparasites and animal subjects, and the inventors intend that their invention will have such applicability.

In the following description and the claims, it is intended that a reference to a percentage means percent by weight, unless the context clearly indicates otherwise. Since the chemical names for certain composition ingredients are quite cumbersome, some ingredients are identified herein by their adopted names as given in standard reference works, including J. A. Wenninger et al, Eds., *International Cosmetic Ingredient Dictionary and Handbook*, $8^{th}$ Ed., The Cosmetic, Toiletry and Fragrance Association, Washington, D.C., 1999.

The present invention extends the observed phenomenon of head lice mobility impairment when their environmental temperature deviates significantly from about 32° C. Nearly complete mortality occurs from exposure to temperatures of about 46° C. for several minutes, and a decrease in mobility is seen when the environmental temperature is reduced below about 30° C. Since such elevated or lowered skin temperatures are easily tolerated by humans and most animals, the inventors determined that ectoparasites can be readily removed from the body by simple mechanical means, such as combing with a fine-tooth comb, while the parasites are immobilized. It is generally preferred that the elevated or reduced temperatures be maintained during the combing process, to prevent individual parasites from simply evading the comb if they regain their mobility. The duration of combing will vary, depending upon a subject's hair density, texture and length, and sometimes amounts to several hours.

Lice egg cases ("nits") are thought to be attached to hair by means of mucopolysaccharide adhesive substances. Removal of the nits therefore requires a very thorough combing operation, and is not appreciably facilitated by many of the usual pesticide treatments. However, one embodiment of the present invention provides both moisture and heat which tend to degrade the adhesive and facilitate nit removal by combing, as well as probably providing the effects of desiccation and an increased pH in the microenvironment of the nit, both of which are thought to alter the physical and chemical nature of the egg casing itself. Providing lubricious agents in a composition also can facilitate lice and nit removal by combing.

The presence of a desiccating microenvironment about the live lice can cause rapid mortality, as evidenced by physiologic changes in the organisms under microscopic observation. These changes include collapsing of the abdomen. Another property of the self-heating compositions of the present invention which is postulated to affect lice mobility and mortality is an elevation of the microenvironmental pH. The active ingredients for heat generation should create high pH regions on their surfaces, during the hydration reaction; it is likely that ectoparasites do not readily tolerate such conditions and are adversely impacted by the high pH. Of course, it is not possible to measure the actual pH conditions at the particle surface, but this surface pH value is likely to be quite different from the bulk pH of the composition.

Elevated temperatures sufficient for inhibiting the mobility of ectoparasites on the human head can be generated and maintained using various means, such as heated combs and brushes, forced heated air, the application of heated liquids and cap-like devices having a relatively thin chamber over its surface for holding a heated substance, most conveniently hot water or a microwave-susceptible fluid. An appropriate device, for example, can structurally resemble a hot water bottle and be molded from a polymeric substance, in the shape of a shower cap. Such devices will provide adequate temperatures for initially immobilizing the lice, but must be removed for the subsequent combing operation and therefore may not provide a sustained temperature condition. However, if the subject's hair is sufficiently short, and therefore not requiring a prolonged combing, it is possible to adequately treat an ectoparasite infestation using such devices.

The inventors prefer to generate elevated temperatures on hair-covered body surfaces, using compositions which contain substances that undergo hydration reactions in an exothermic manner. Such compositions have an advantage, in that they can be formulated to generate heat, then remain in place while the mechanical removal of immobilized and killed parasites is effected.

Suitable self-heating compositions for use in the invention generally are non-aqueous in nature, or have only a very small water content, and contain as their active ingredient a substantially anhydrous inorganic component such as a silica, an aluminosilicate, an alkaline earth metal oxide or a combination of such components, which exhibits an exothermic reaction upon contact with water. To maximize heat evolution when the active ingredient contacts water, and to facilitate combing of hair with the composition in place, it is preferred to use particles of the active ingredients having average sizes in the range of about 3 $\mu$m to about 6 $\mu$m. However, particles having larger or smaller sizes will function adequately in the invention.

Particulate inorganic substances which are useful in the compositions of the invention include materials such as fumed silica, aluminosilicates, aluminum oxide, magnesium oxide and calcium oxide. Typically, the inorganic particulate will be present in a composition in amounts about 1 percent to about 65 percent. The use of aluminosilicates is presently preferred and these include materials commonly known as "zeolites."

Zeolites suitable for use in the invention include both the naturally occurring materials and the synthetically produced materials. Zeolites have typically been used as ion-exchange agents, adsorbents for gaseous and liquid chemical substances and as supports for catalysts, such as the catalysts used in petroleum refining. For use in the present invention, the zeolites are "activated" by removal of their crystalline water content; this is accomplished by heating to relatively high temperatures until the desired water content is obtained, the temperature and duration of heating necessarily being individually determined for each type of zeolite. Presently commercially available activated zeolites that are useful in the invention include, without limitation: MOL-SIV™ products sold by UOP LLC of Des Plaines, Ill. USA and identified as Type 3A (potassium aluminosilicate), Type 4A (sodium aluminosilicate) and Type 5A (calcium aluminosilicate). Products being sold by W. R. Grace & Co. of Columbia, Md. U.S.A. under the trademark SYLOSIV are other examples of useful zeolites. Some zeolites are aluminosilicates of mixed alkali metals and/or alkaline earth metals, and these are also well-suited for use in the present invention.

Suitable compositions can be in the forms of a dry powder, a lotion or cream, or a fluid pressurized aerosol. The most simple self-heating compositions frequently will be the dry powders, since the only essential component is the particulate active ingredient; other components, such as dry surfactants, may be added to facilitate combing such as when the composition is applied to moistened hair.

To prepare a preferred fluid form of a self-heating ectoparasite removal composition, including a lotion, cream or aerosol form, the heat-generating inorganic particulate may be suspended in a substantially anhydrous vehicle, such as: a light or heavy mineral oil; a glycol such as polyethylene glycol, propylene glycol or triethylene glycol; glycerol; and the like. Typical concentrations of the vehicle range from about 1 percent to about 60 percent. Selection of the vehicle can affect the heat generation reaction, since a more water-impervious substance such as mineral oil can impede access of water to the particulate solid, and thereby slow the rate of temperature increase and/or the maximum temperature obtained.

It is generally desired to achieve temperatures above about 37° C. to maximize efficacy, but to limit the maximum temperature attained by the formulation to about 55° C., to avoid discomfort when applied to the body.

Optionally, a suspending agent may be present in the self-heating composition to maintain a more stable dispersion. Useful agents include, without limitation, fumed silica and polyvinylpyrrolidone having molecular weights from about 25,000 to about 100,000, in amounts about 0.1 to about 2 percent.

The compositions may further include other components, such as surfactants, lubricants, texture modifiers, acidifiers, preservatives and other cosmetic-type ingredients used to create desired physical properties.

Useful optional surfactants include, without limitation, sodium lauryl sulfate, sorbitan laurate, mixtures of glyceryl stearate and PEG-100 stearate, methyl gluceth-10, methyl gluceth-40, sorbitan palmitate, polysorbate 20, polysorbate 80, steareth-2 and many others. The surfactants will be present in amounts about 0.1 to about 16 percent, and can create shampoo-type products which are easily removed after the ectoparasite treatment is completed.

The lubricants that can be incorporated are represented by dimethicone, simethicone and other silicone-type materials, and act to lubricate and condition the hair, as well as facilitate passage of a comb through the hair. Useful concentrations, when this component is present, are about 0.1 to about 2 percent.

Optional texture modifiers that may be included are exemplified by stearic acid, cetyl alcohol, PEG-180, polyethylene glycol 1450 and polyethylene glycol 3350, in amounts about 0.1 percent to about 5 percent.

It may be desired to incorporate an acidic ingredient in the composition, since the heat-generating active ingredients tend to produce alkaline suspensions in water. Optional acidifiers that may be used include, without limitation, benzoic acid, citric acid and stearic acid. It is preferred to use anhydrous acidifiers. The acids will generally be present in amounts about 0.1 percent to about 2 percent, as needed to obtain a desired bulk pH condition when the compositions are used.

Products that are intended for application to the skin frequently are protected against microbial proliferation by the inclusion of a preservative component. Suitable preservatives for use in the present compositions include, without limitation, methylparaben, propylparaben and benzethonium chloride. The preservative will typically be included in concentrations about 0.05 to about 0.2 percent.

Included within the scope of the present invention is a kit for treating an ectoparasite infestation, including a suitable container filled with a composition that can be applied to an area of the body to reduce or increase the temperature of the area, together with a mechanical device for removing ectoparasites after they are affected by the composition. For compositions that are in the form of a fluid, such as liquids, lotions and creams, the composition can be contained in a bottle or collapsible tube. Aerosol compositions can be contained in the customary dispensing canisters, fitted with a suitable valve for dispensing the product. Powdered compositions can be contained in one of the customary canisters having a perforated cap for shaking out a desired amount, or in a bottle. Many delousing combs are commercially available, being fabricated from plastic substances or metals, and any of these are suitable for inclusion in the kit. It is preferred that the kit be made suitable for a single use, including sufficient composition for one application.

The invention will be further described with reference to the following examples, which are not intended to limit the scope of the claimed invention in any manner.

EXAMPLE 1

Cream and lotion compositions for ectoparasite removal which generate heat upon contact with water are prepared by combining the following components:

| No. | Ingredient | Wt. Percent |
| --- | --- | --- |
| 1 | Sodium aluminosilicate | 35 |
|   | Triethylene glycol | 48 |
|   | Sodium lauryl sulfate | 16 |
|   | PEG-180 | 1 |
| 2 | Sodium aluminosilicate | 65 |
|   | PEG-4 | 17 |
|   | Triethylene glycol | 18 |
| 3 | Sodium aluminosilicate | 40 |
|   | Fumed silica | 0.5 |
|   | Cetyl alcohol | 0.2 |
|   | Dimethicone | 1 |
|   | PEG-400 | 58.1 |
|   | Polyvinylpyrrolidone | 0.1 |
|   | Stearic acid | 0.1 |
| 4 | Potassium aluminosilicate | 40 |
|   | Fumed silica | 0.5 |
|   | Cetyl alcohol | 0.2 |
|   | Dimethicone | 1 |
|   | PEG-400 | 58.1 |
|   | Polyvinylpyrrolidone | 0.1 |
|   | Stearic acid | 0.1 |
| 5 | Potassium aluminosilicate | 45 |
|   | Heavy mineral oil | 12 |
|   | Propylene glycol | 12 |
|   | Glycerin | 2 |
|   | Polysorbate 80 | 10 |
|   | Glyceryl stearate + PEG-100 stearate* | 2 |
|   | Sorbitan laurate | 10 |

-continued

| No. | Ingredient | Wt. Percent |
|---|---|---|
|  | Methyl gluceth-20 | 5 |
|  | Dimethicone | 2 |
| 6 | Potassium aluminosilicate | 40 |
|  | PEG-400 | 25.3 |
|  | PEG-600 | 25.6 |
|  | Polyvinylpyrrolidone | 0.1 |
|  | Dimethicone | 1 |
|  | Cetyl alcohol | 0.3 |
|  | Stearic alcohol | 0.3 |
|  | Polysorbate 20 | 5 |
|  | Fumed silica | 0.2 |
|  | Benzoic acid | 2 |
|  | Methylparaben | 0.13 |
|  | Propylparaben | 0.07 |

*Arlacel ™ 165, sold by Uniquema, New Castle, Delaware U.S.A.

Composition 6 is prepared as follows: (1) the PEG-400 is heated to about 60° C. and stirred while the polyvinylpyrrolidone is slowly sprinkled onto the liquid surface, then stirring is continued until a solution has been formed; (2) in a separate vessel, the PEG-600, cetyl alcohol and stearic acid are stirred and heated to about 60° C. to form a solution; (3) the solution of step 1 is added to the solution of step 2 with thoroughly stirring, while maintaining the temperature about 60° C.;(4) the benzoic acid, methylparaben and propylparaben are sequentially added with continued stirring and maintenance of the 60° C. temperature condition, each component being completely dissolved before the next is added; (5) with continued stirring and temperature maintenance, the dimethicone, polysorbate 20 and fumed silica are added; and (6) the potassium aluminosilicate is added, heating is discontinued, and stirring is continued to assure a uniform dispersion as the mixture cools to ambient temperature.

EXAMPLE 2

Some compositions of the preceding example are tested to determine the increases in temperature that can be obtained by mixing them with water. A portion of a composition is placed in a foamed polystyrene cup, the desired amount of water is added and the temperature of the mixture is recorded as a function of time, while the mixture is being stirred. All materials used are initially equilibrated to a room temperature of about 24° C., or are initially at a temperature about 32° C., simulating that of the human scalp. The following results are obtained:

| Composition Number | Composition Weight, grams | Water Weight, grams | Time, seconds | Temperature, ° C. |
|---|---|---|---|---|
| 3 | 25 | 1 | 0 | 32 |
|  |  |  | 30 | 55 |
|  |  |  | 60 | 53 |
|  |  |  | 90 | 49 |
|  |  |  | 120 | 47 |
|  |  |  | 150 | 50 |
|  |  |  | 180 | 48 |
| 4 | 30 | 1 | 0 | 32 |
|  |  |  | 10 | 50 |
|  |  |  | 20 | 55 |
|  |  |  | 30 | 56 |
|  |  |  | 40 | 56 |
|  |  |  | 50 | 54 |
|  |  |  | 60 | 52 |
|  |  |  | 90 | 50 |

-continued

| Composition Number | Composition Weight, grams | Water Weight, grams | Time, seconds | Temperature, ° C. |
|---|---|---|---|---|
|  |  |  | 120 | 53 |
|  |  |  | 180 | 45 |
| 6 | 25 | 5 | 0 | 24 |
|  |  |  | 15 | 50 |
|  |  |  | 30 | 63 |
|  |  |  | 45 | 65 |
|  |  |  | 60 | 64 |
|  |  |  | 75 | 61 |
|  |  |  | 90 | 60 |
|  |  |  | 105 | 59 |
|  |  |  | 120 | 57 |
|  |  |  | 180 | 52 |
|  |  |  | 240 | 49 |
|  |  |  | 300 | 46 |

EXAMPLE 3

A pressurized aerosol composition which generates heat upon contact with water is prepared by combining the following components, and sealing the mixture in an aerosol canister equipped with a dispensing valve.

| Ingredient | Wt. Percent |
|---|---|
| Sodium aluminosilicate | 47 |
| Propylene glycol | 43.2 |
| Emulsifying wax NF* | 1.9 |
| Oleth-2 | 1.9 |
| Methyl gluceth-20 | 1.9 |
| Isobutane | 6 |

*Polawax A-31 sold by Croda, Inc. of Parsippany, New Jersey U.S.A.

EXAMPLE 4

Pressurized aerosol compositions for ectoparasite removal which can produce low temperatures when dispensed are prepared by combining the listed components. When dispensed through an aerosol valve into a foamed polystyrene cup, the indicated temperatures are observed. The compositions can be applied to ectoparasite-infested areas to immobilize the pests.

| No. | Ingredient | Wt. Percent | ° C. |
|---|---|---|---|
| 1 | n-Butane | 50.63 | −12 |
|  | Cocoa butter | 1.5 |  |
|  | PEG-1450 | 0.5 |  |
|  | Glycerin | 12.5 |  |
|  | Propylene glycol + Glyceryl oleate* | 1.5 |  |
|  | Zinc oxide | 1.5 |  |
|  | White petrolatum | 13.37 |  |
|  | Stearalkonium hectorite | 1 |  |
|  | Water | 17.5 |  |

*Arlacel ™ 186 sold by Uniqema, New Castle, Delaware U.S.A.
**Bentone ™ 27CG sold by Rheox, Inc., Hightstown, New Jersey U.S.A.

| | | | |
|---|---|---|---|
| 2 | Isopentane | 35 | −8 |
|  | Alcohol SD-40-2 | 12 |  |
|  | Cetearyl alcohol + Ceteareth-20* | 3 |  |
|  | Isobutane | 35 |  |
|  | Water | 15 |  |

*Promulgen ™ D sold by Amerchol Corporation, Edison, New Jersey U.S.A.

| | | | |
|---|---|---|---|
| 3 | Dimethyl ether | 30.88 | 0 |
|  | Dimethicone, 350 centistokes | 1 |  |

-continued

| No. | Ingredient | Wt. Percent | ° C. |
|---|---|---|---|
| | Glycerin | 16.5 | |
| | Propylene glycol + Glyceryl oleate* | 5 | |
| | Sono Jell ™** | 4.5 | |
| | Zinc oxide | 2 | |
| | Petrolatum | 20 | |
| | Stearalkonium hectorite*** | 1 | |
| | Water | 19.12 | |

*Arlacel ™ 186 sold by Uniqema, New Castle, Delaware U.S.A.
**Petrolatum, sold by Crompton, Greenwich, Connecticut U.S.A.
***Bentone ™ 27CG sold by Rheox, Inc., Hightstown, New Jersey U.S.A.

EXAMPLE 5

Composition 6 of preceding Example 1 is tested with human subjects infested with *Pediculus humanus* var *capitis*, to measure its efficacy as an agent for pest removal. In the test, 30 subjects are initially inspected to verify the presence of a head lice infestation and then are treated as follows: the hair is wetted thoroughly with warm water, the composition is applied in amounts of 100 grams (for subjects having hair between about 10 to 20 cm in length) or 200 grams (for subjects having hair lengths between about 20 to 30 cm in length) and massaged throughout the hair for a few minutes, then the composition is allowed to remain on the hair undisturbed for about ten minutes while lice mobility is evaluated. Without removing the composition, the hair is combed, first with a wide-toothed comb to eliminate hair tangling and remove lice and then with a metal-toothed lice comb to remove lice and nits. The combs are wiped and rinsed as needed to eliminate comb tooth clogging by the composition. After the combing procedure, the subjects' hair is washed with a gentle shampoo and dried with a towel, then an inspection is performed to determine if any lice and nits remain on the subject.

After 7 to 10 days, the subjects are again inspected to determine the presence of lice and nits, and then the entire treatment of the preceding paragraph is repeated. At 14 days following the first treatment (the end of the study), the subjects are inspected to detect any remaining lice or nits.

No live lice are visually detected on any subject immediately following either of the two treatments. Lice are partially to fully immobilized on 29 of the subjects (97%) during the first treatment. During the treatment, lice are seen to cease movement and, under microscopic observation, have collapsed abdomens and an absence of noticeable peristalsis of the gut. Viable nits appear to swell during the treatment; this can facilitate their removal by combing. There are varying numbers of visible nits present on 23 subjects after the first treatment. Before the second treatment, 20 subjects have live lice in their hair, possibly due at least in part to hatching of residual nits from the first treatment. At the end of the study (14 days following the first treatment), 26 of the subjects (87%) are determined to be completely free of lice and 27 of the subjects (90%) are completely free of viable nits.

From this description of specific embodiments of the invention, it will be appreciated that the present invention is not limited to those precise embodiments and that various changes and modifications can be effected therein by one of ordinary skill in the art, without departing from the scope or spirit of the invention as defined by the appended claims. In addition, certain theories have been proposed to enhance the understanding of the invention, but it is not intended to restrict the invention to any particular theory of operation.

What is claimed is:

1. A method for treating an ectoparasitic infestation of an area of a human or animal body, comprising applying to a previously or subsequently moistened area a substantially anhydrous fluid composition containing a particulate water-insoluble inorganic substance that reacts exothermically with water to produce elevated temperatures for a time sufficient to immobilize or kill ectoparasites, and mechanically removing affected ectoparasites.

2. The method of claim 1, wherein the ectoparasites comprise *Pediculus humanus* var *capitis*.

3. The method of claim 1, wherein the ectoparasites comprise *Pediculus humanus* var *corporis*.

4. The method of claim 1, wherein the ectoparasites comprise *Pediculus humanus* var *pubis*.

5. The method of claim 1, wherein the ectoparasites comprise fleas, ticks or mites.

6. The method of claim 1, wherein the ectoparasites are removed by combing.

7. The method of claim 1, wherein the composition is applied to a previously moistened area.

8. The method of claim 1, wherein an active ingredient in the composition comprises a particulate substantially a hydrous silica, aluminosilicate, alkaline earth metal oxide or a combination of two or more thereof.

9. The method of claim 1, wherein an active ingredient in the composition comprises a particulate substantially anhydrous aluminsilicate.

10. The method of claim 1, wherein the composition is in the form of a powder, lotion, cream or fluid pressurized aerosol.

11. The method of claim 1, wherein temperatures at least about 37° C. are produced.

12. The method of claim 1, wherein temperatures between about 37° C. and about 55° C. are produced.

13. The method of claim 1, wherein affected ectoporasites are removed by combing.

14. A method for treating an ectoparasitic infestation of an area of a human or animal body, comprising the steps of: moistening an area to be treated, with water; applying to the moistened area a substantially anhydrous fluid composition containing an amount of a particulate water-insoluble inorganic substance that reacts exothermically with water, sufficient to create an elevated temperature for a time resulting in immobilization or death of ectoparasites; and mechanically removing affected ectoparasites.

15. The method of claim 14, wherein a temperature at least about 37° C. is established.

16. The method of claim 14, wherein a temperature between about 37° C. and about 55° C. is established.

17. The method of claim 14, wherein temperatures between about 37° and about 55° are maintained for sufficient time to kill or immobilize ectoparasites.

18. The method of claim 14, further comprising the step of removing killed or immobilized ectoparasites by combing.

19. The method of claim 14, wherein the composition is a lotion, cream or pressurized aerosol.

20. A method for treating an ectoparasitic infestation of an area of a human or animal body, comprising applying to a water-moistened area a substantially anhydrous fluid composition containing a particulate water-insoluble aluminosilicate that reacts exothermically with water to produce temperatures at least about 37° C. for a time sufficient to immobilize or kill ectoparasites, and mechanically removing affected ectoparasites.

* * * * *